US012582795B2

(12) United States Patent
Miller et al.

(10) Patent No.: US 12,582,795 B2
(45) Date of Patent: Mar. 24, 2026

(54) GAS FLOW CONTROLLER AND A VALVE PIN FOR A GAS FLOW CONTROLLER

(71) Applicant: INTERSURGICAL AG, Vaduz (LI)

(72) Inventors: Andrew Miller, Bracknell (GB); Mark Browne, Wokingham (GB); Philip Dixon, Wokingham (GB)

(73) Assignee: INTERSURGICAL AG, Vaduz (LI)

( * ) Notice: Subject to any disclaimer, the term of this patent is extended or adjusted under 35 U.S.C. 154(b) by 1004 days.

(21) Appl. No.: 16/961,095

(22) PCT Filed: Jan. 10, 2019

(86) PCT No.: PCT/EP2019/050598
§ 371 (c)(1),
(2) Date: Jul. 9, 2020

(87) PCT Pub. No.: WO2019/138020
PCT Pub. Date: Jul. 18, 2019

(65) Prior Publication Data
US 2020/0353202 A1 Nov. 12, 2020

(30) Foreign Application Priority Data
Jan. 10, 2018 (GB) ..................................... 1800394

(51) Int. Cl.
*A61M 16/12* (2006.01)
*A61M 16/00* (2006.01)
(Continued)

(52) U.S. Cl.
CPC .......... *A61M 16/12* (2013.01); *A61M 16/024* (2017.08); *A61M 16/1005* (2014.02);
(Continued)

(58) Field of Classification Search
CPC ................ A62B 9/02; A61M 2205/10; A61M 16/20–209; A61M 16/12; A61M 16/022;
(Continued)

(56) References Cited

U.S. PATENT DOCUMENTS

| | | | |
|---|---|---|---|
| 2,516,825 A | * | 7/1950 | Hejduk ..................... F16K 3/34 251/903 |
| 3,511,470 A | | 5/1970 | Beckett et al. |

(Continued)

FOREIGN PATENT DOCUMENTS

| | | |
|---|---|---|
| CN | 103 591 351 A | 2/2014 |
| EP | 2489392 A1 | 8/2012 |

(Continued)

OTHER PUBLICATIONS

Search Translation of KR950009539Y1 (Year: 1995).*
(Continued)

*Primary Examiner* — Valerie L Woodward
*Assistant Examiner* — Mautin I Ashimiu
(74) *Attorney, Agent, or Firm* — Troutman Pepper Locke LLP (Rochester)

(57) ABSTRACT

The invention relates to gas flow controllers, for example to gas blender units such as an air/oxygen blender (2) for healthcare use, and to a valve (8) and valve pin (20,120) suitable for use in such a flow controller (20). In particular, a medical gas blender (2) is provided that avoids the need for pre-regulation by incorporating one or more flow control valves (8) having a high turndown ratio. Valves suitable for use in such a blender, or other flow controller (2), are also disclosed.

24 Claims, 11 Drawing Sheets

148

145

152A

152B

(51) Int. Cl.

| | |
|---|---|
| *A61M 16/10* | (2006.01) |
| *A61M 16/20* | (2006.01) |
| *F16K 1/36* | (2006.01) |
| *F16K 1/54* | (2006.01) |
| *F16K 31/04* | (2006.01) |
| *G05D 11/13* | (2006.01) |

(52) U.S. Cl.

CPC ... *A61M 16/202* (2014.02); *A61M 2016/0039* (2013.01); *A61M 2016/1025* (2013.01); *A61M 2205/3334* (2013.01); *A61M 2205/8206* (2013.01)

(58) Field of Classification Search

CPC ........ A61M 16/024; F16K 31/04; F16K 1/52; F16K 1/54; F16K 3/32–34; F16K 5/10; F16K 5/103; F16K 5/12

See application file for complete search history.

(56) References Cited

U.S. PATENT DOCUMENTS

| | | | | |
|---|---|---|---|---|
| 3,875,968 A * | 4/1975 | Olofsson | ............... | G05D 11/03 |
| | | | | 137/636.1 |
| 5,544,674 A | 8/1996 | Kelly | | |
| 5,887,611 A * | 3/1999 | Lampotang | ........... | A61M 16/12 |
| | | | | 137/93 |
| 5,901,746 A * | 5/1999 | Andersson | ............... | F16K 1/54 |
| | | | | 137/861 |
| 6,321,780 B1 | 11/2001 | Iwabuchi | | |
| 6,953,056 B1 * | 10/2005 | Chrisp | ..................... | F16K 1/54 |
| | | | | 137/625.33 |
| 7,757,711 B2 * | 7/2010 | Hama | .................. | G05D 7/0146 |
| | | | | 137/601.19 |
| 2005/0205140 A1 * | 9/2005 | Hull | .................... | G05D 7/0126 |
| | | | | 137/613 |
| 2008/0011362 A1 * | 1/2008 | Hama | .................. | G05D 7/0146 |
| | | | | 251/264 |
| 2010/0170512 A1 * | 7/2010 | Kuypers | ........... | A61M 16/0069 |
| | | | | 128/204.23 |
| 2012/0318263 A1 | 12/2012 | Jones et al. | | |
| 2013/0220737 A1 * | 8/2013 | Divisi | ...................... | F16K 1/38 |
| | | | | 184/7.4 |
| 2014/0103235 A1 * | 4/2014 | Xu | ........................... | F16K 3/34 |
| | | | | 251/118 |
| 2017/0344030 A1 * | 11/2017 | Kirchner | .............. | G05D 7/0133 |
| 2018/0214649 A1 * | 8/2018 | Peller | .................. | A61M 16/024 |

FOREIGN PATENT DOCUMENTS

| | | | | | |
|---|---|---|---|---|---|
| EP | 3249269 A1 | * | 11/2017 | .............. | F16K 1/36 |
| GB | 1 429 435 A | | 3/1976 | | |
| GB | 1577506 A | | 10/1980 | | |
| GB | 2 485 417 A | | 5/2012 | | |
| JP | S60-263784 | | 12/1985 | | |
| JP | 2001-4062 | | 1/2001 | | |
| KR | 950009539 Y1 | * | 11/1995 | | |
| KR | 200376936 Y1 | * | 3/2005 | | |
| WO | 98/29154 A1 | | 7/1998 | | |
| WO | 98/37343 A2 | | 8/1998 | | |

OTHER PUBLICATIONS

Machine Translation of KR_200376936_Y1 (Year: 2005).*
PCT International Preliminary Report on Patentability for corresponding Application No. PCT/EP2019/050598 (mailed Jul. 14, 2020).
US 5,677,167, A, Kelly, (withdrawn)
International Search Report and Written Opinion for corresponding Application No. PCT/EP2019/050598 (mailed Mar. 22, 2019).
Great Britain Search Report for corresponding Application No. GB1800394.7 (mailed Jun. 18, 2018).
Great Britain Search Report for corresponding Application No. GB1900366.4 (mailed Jul. 16, 2019).
Great Britain Search Report for corresponding Application No. GB1900366.4 (mailed Jan. 17, 2020).

* cited by examiner

120

152A

144

145

152A

L4

L5

152B

148

GAS FLOW CONTROLLER AND A VALVE PIN FOR A GAS FLOW CONTROLLER

This application is a national stage application under 35 U.S.C. § 371 of PCT Application No. PCT/EP2019/050598, filed Jan. 10, 2019, which claims the priority benefit of Great Britain Patent Application No. 1800394.7, filed Jan. 10, 2018.

The present invention relates to a gas flow controller such as a gas blender unit, for example an air/oxygen blender for healthcare use, and to a valve and valve pin for use in such a flow controller.

Air/Oxygen blenders are known for use in a variety of healthcare applications to offer a reliable and accurate method of delivering the gas to the patient. Fixed lines at a wall of a hospital provide gases at a high pressure typically between 2 and 6 bar, and these gases need to be mixed in desired proportions and delivered to a patient at a particular pressure and/or flow rate.

Medical gas devices that are driven from high pressure air and oxygen typically fall into two categories:

1. Medical ventilators, which use a pressure regulator to drop the incoming range or pressure to a reliable predetermined value, so that a precise response to changes in the valve position can be calculated allowing rapid and predictable changes in flow; and 2. Medical flow meters, which use a precision machined pin in an aperture to control the flow, the pin and valve being controlled to very tight dimensions using a fine screw thread which moves the pin in and out.

The ability to provide precisely mixed air and oxygen in a safe, easy and controlled manner is becoming increasingly important, particularly in critical care and therapeutic care of premature infants, where there are severe consequences associated with the supply of either too little or too much oxygen. Accordingly, known gas blender systems are typically developed based on a mechanical ventilator, with a regulator to moderate the gas pressure from the wall before the mixing and delivery function is performed.

The accuracy of mechanical ventilator systems makes them particularly suitable for modification for use as gas blenders. However, unnecessary complexity often remains even after modification or simplification of a mechanical ventilator, and a first stage pressure regulator is required to drop the input pressure prior to the final flow control. This leads to unnecessary cost and complexity in the final gas blender, which does not need the millisecond response times the ventilator arrangement is designed for.

A medical flow meter does not typically have a pressure regulator to reduce the initial flow pressure, but still needs to be able to give sufficient control when both low flows at high driving pressures, and high flows at low driving pressures, are required. This is achieved by the fine screw thread, meaning that many turns of the thread are required to show any movement or change in flow when operating at the high flow/low driving pressure end. This reduces the responsiveness of the valve, impeding the ability of a flow meter to respond to sudden fluctuations in supply pressure or to adjust an output flow rate rapidly as might be required, for example, in a gas blender application. Although the supply of gas from the wall in hospitals is regulated by an ISO standard, and supply is generally between 2 and 6 bar, there are situations where there are pressure fluctuations in the wall supply. A desire existed, therefore, for a simpler more cost-effective gas blender unit which retained the benefits responsive flow control over a range of flow rates.

This desire led to a complete re-assessment of the process of designing a medical gas blender. It was determined that through including an improved flow control valve, with a high turndown ratio, a system could be provided which could overcome or help to mitigate the problems identified above.

All valves have a certain :turndown ratio", defined as the ratio of maximum to minimum flow. In most instances, valves provided in mechanical ventilators and similar generally have a turndown ratio of up to or around 100:1. That is to say the valve provides accurate flow output between, for example, 1 lmin$^{-1}$ and 100 lmin$^{-1}$. At a fixed driving pressure this can provide control at suitable accuracy over a range of, for example, 0.5 lmin$^{-1}$ to 50 lmin$^{-1}$. It would not be capable of providing that control if the driving pressure were varied from 2 to 6 bar, i.e. without pre-regulation. The remaining aspects of a gas blender can be greatly simplified through the use of a valve with a considerably higher turndown ratio. The proposed design offers ratios in excess of 1000:1, allowing a simple gas blender to be provided which allows both the 'active' regulation and simultaneous metering of a gas with no need for a first stage regulation of flow pressure upstream of the mixing step.

The development of the invention came from a realisation that the conventional approach to the design of gas flow controllers, in particular controllers for medical applications such as gas blenders, was fundamentally flawed. Moving away from the accepted development process allowed the consideration of design options that would not have otherwise been considered.

According to the present invention there is provided a medical gas blender as defined in the appended claim 1. Further optional features are recited in the associated dependent claims.

The gas blender comprises a first inlet for connection to a first gas supply, a second inlet for connection to a second gas supply, a mixing chamber, a first flow regulation valve located between the first inlet and the mixing chamber for controlling the flow of a first gas to the mixing chamber, a second flow regulation valve located between the second inlet and the mixing chamber for controlling the flow of a second gas to the mixing chamber, an outlet, and control hardware for controlling the operation of at least one of the first and second flow regulation valves, wherein the first and second flow regulations valves have a turndown ratio in excess of 1000:1. The gas blender may further comprise an oxygen sensor.

The control hardware may be configured to perform a measuring step, in which a gas flow is measured, and a comparison step, in which the measured gas flow is compared with a target flow.

The control hardware may be configured to select a gas flow prior to the measuring step.

The control hardware may be configured to additionally measure oxygen content and calculate individual gas flows as part of the measuring step.

At least one of the first and second flow regulation valves may comprise a valve member driven by a motor, and the control hardware may be configured to move the motor a number of steps based on the outcome of the comparison step.

The valve member may comprise a valve pin or may comprise rotating discs.

The valve pin may comprise an elongate body with a first end and a second, free, end remote from the first end, an outer sealing surface and a tapered part tapering towards the second end of the body, wherein a sealing position (at which the valve pin may form a complete gas-tight seal with a sealing element such as an o-ring or similar) is provided towards the first end of the valve body, and the valve pin may be shaped to increase the flow area of the valve close to the sealing position.

For example, a recess may be provided in the outer sealing surface of the body close to the sealing position.

The recess may comprise an elongate channel or slit, the length of the slit being aligned with the length of the elongate body.

The depth of the elongate slit may vary along the length of the slit.

The outer sealing surface may have a substantially constant cross-section, and the tapered part of the body may be provided by the variation in depth of the elongate slit.

The elongate slit may be flared towards the free end of the body, in width and/or in depth.

The slit may provide an open end section at the free end of the body.

The tapered part of the body may comprise a tapering of the outer sealing surface at the second end such that the body of the valve pin has a first portion of substantially constant cross-section and a second separate portion tapered towards the free end, the sealing position being provided on the first portion.

More than one recess, for example first and second elongate slits, may be provided. The length of the first and second elongate slits may be similar, or the length of the first elongate slit may be greater than the length of the second elongate slit.

Also provided is a gas flow controller as defined in the appended claims.

The gas flow controller is a simpler construction than the gas blender previously described, and comprises a flow regulation valve with a valve pin and a sealing element surrounding the valve pin to provide a seal between the sealing element and the valve pin at a sealing position on the valve pin. Relative movement of the valve pin and the sealing element away from the sealing position adjusts the gas flow through a range of flow rates and/or pressures.

A typical mechanical ventilator includes control valves and associated control architecture to govern the gas composition and flow rate as well as other functions allowing the ventilator to adjust, rapidly, to changes in a patient.

While the precise flow control provided by mechanical ventilators is clearly beneficial in gas blender applications, several of the more complex control functions also provided by a typical ventilator are unnecessary. It is possible for some of the redundant or unnecessary control systems or features to be removed or inhibited when producing a gas blender device, but the resulting systems still tend to be overcomplicated, and therefore costly. For example, the rapid response provided by proportional solenoid valves, or similar, is not required in typical steady flow gas blender applications.

Through the resulting development of a suitable valve pin, a gas blender can provide the necessary precision of flow rate control in a simple package and operate across a wide range of pressures, without the need for a pressure regulator to be provided upstream of or built into the device, whilst still delivering a very controlled oxygen concentration in the gas mix.

The valve pin may be shaped, for example in cross-section, to increase the cross-sectional area of the valve, ie the flow area through the valve, close to the sealing position. Increasing the cross-sectional area helps to control the flow through the valve at a near-sealed position, ie when the sealing position on the surface of the valve pin is close to a sealing element such as an O-ring.

An outer sealing surface of the valve pin may comprise a recess, such as an elongate slit or channel to increase the cross-sectional area and/or provide or increase the flow area of a path through the valve at a near-sealed position. More than one recess may be provided.

An elongate slit may be provided between a free end of the valve pin and the sealing position. For example, the slit may terminate at the free end of the valve pin and/or adjacent the sealing position.

The depth of the elongate slit, into the valve pin, may vary along the length of the slit. For example, the depth of the elongate slit may reduce from the free end of the valve pin towards the sealing position. Alternatively, the depth may fluctuate along the length, if this provides the necessary adjustment of cross-section for a particular application.

The width of the elongate slit may be constant along the length of the slit. Alternatively, the width of the slit could vary, if required, to provide additional adjustment to the cross-sectional area of the valve.

The recess need not take the form of a slit, and may instead be an alternative shape. Where multiple recesses are provided, they need not all be of a consistent shape, size, length etc. For example, a single pin could have two or more slits of different lengths and possibly a further generally circular recess. Alternatively, or additionally, multiple slits could be provided each of which have different widths and/or different internal profiles (decreasing/fluctuating/ constant depths or widths, etc).

Alternatively, some kind of texture or minute surface modification, for example small protrusions or ridges, could be provided adjacent the sealing position. The texturing may provide recessed paths in the surface of the valve pin, or raised features could deform parts of an O-ring or similar sealing element and lift it clear of the sealing surface of the valve pin to the pin to provide or increase a flow area between the valve pin and the sealing element.

The gas flow controller may further comprise a linear stepper motor connected to the valve pin for moving the valve pin relative to the sealing element. The stepper motor may be connected at an end of the valve pin opposite the free end.

The valve pin may have a substantially circular cross-section. A flat section may then be provided in place of, or in addition to, a recess or texture/protrusion to provide or increase a flow area between the valve pin and the sealing element.

The valve pin may comprise a taper towards the free end. The valve pin may be tapered along its entire length, or may have a first un-tapered section, or section of substantially constant cross-section, and a second tapered section towards the free end to provide a :bullet˘shape. The cross-section of the valve pin can, for these purposes, be considered excluding any slit/recess or protrusion.

The sealing position may be located on the first section of the valve pin.

The elongate slit may be aligned with a plane passing through the axis of the, eg substantially circular, cross-section of the valve pin.

The gas flow controller may be a medical gas flow controller, ie a controller for use in a hospital or other medical environment.

For example, the gas flow controller may be a simple medical flow meter, or it may be a medical gas blender, such as an air/oxygen blender, comprising a mixing chamber and a flow regulation valve for controlling the gas flow from a gas supply to the mixing chamber.

Two flow regulation valves may be provided in the gas blender, each flow regulation valve comprising a valve pin and a sealing element surrounding the valve pin to provide a seal between the sealing element and the valve pin at a sealing position on the valve pin, and wherein relative movement of the valve pin and the sealing element away from the sealing position adjusts the gas flow through a range of flow rates. Both valve pins may comprise one or more features as described above, and both may be actuated with a stepper motor.

Actuation of the two valve pins may be independent of one another to allow independent adjustment of two gas flows into the mixing chamber.

The gas flow controller may further comprise an oxygen sensor.

The gas flow controller may further comprise control hardware, for example an electronic controller, to control relative movement of the valve pin and the sealing element. The control hardware may include a feedback loop.

The invention also provides a valve, for use in a medical gas flow controller, as defined in the appended claims.

As previously described, a gas blender is probably more similar to a simplified ventilator than a flow meter, although it could be considered to fit somewhere between the two categories.

In developing the present invention, a valve was developed that provides an increased turndown ratio, making the valve more practical to use when operating across these driving pressure ranges.

As already noted, the valves used in ventilators and similar flow controllers have a turndown ratio which is generally around 100:1. The valve of the present invention has, in some embodiments, been found to increase the turndown ratio to around 1500:1, essentially providing accuracy between, for example, 0.08 lmin$^{-1}$ and 120 lmin$^{-1}$, by combining two flow control mechanisms, namely a tapered pin shape and an increased valve cross-section/flow area near to the closed/sealed position, into one. In other embodiments the valve of the present invention has been found to increase the turndown ratio to around 5000:1, essentially providing accuracy between, for example, 0.025 lmin$^{-1}$ and 125 lmin$^{-1}$. Again, this is achieved by providing an increased valve cross-section/flow area near to the closed/ sealed position and a tapered section of the valve pin, as well as an opening/flaring at the free end of the valve.

In all suitable applications, the improved valve pin addresses the aim of providing the largest possible turndown ratio without including a pressure regulator.

In a flow meter, the valve needs to be capable of delivering high flows at low wall pressures (ie fully open), but also manage and even out any pressure fluctuations (which is where small accurate changes in flow are necessary), particularly where the wall pressure is high but the set flow is low (ie with the valve near its closed position).

As noted above, there are situations where there are pressure fluctuations in the wall supply in hospital environments. In a conventional flow meter, the pressure setting selected by the clinician is static and cannot account for this pressure fluctuation without being manually altered. The valve arrangement and valve pin of the present invention not only allows different wall pressures to be accommodated, but also provides a rapid response that can even out the fluctuations and maintain supply at the selected flow rate.

The fine control may already be provided by certain existing systems and known valve arrangements, but the valve pin and valve of the present invention provides an alternative solution, while also allowing much more rapid reaction to pressure changes. As will be described later, conventional valves tend to provide a sudden increase in flow rate immediately once opened. To provide the necessary control in this region, a fine screw thread is typically provided to allow tiny movements of the valve pin. This, however, reduces the overall responsiveness of the valve. The improved valve pin design provides a more gradual response at low flow rates, so the movement need not be controlled so precisely to provide comparable flow control in this region. This allows faster movement of the valve, and thus faster response across its entire operating range.

In addition, to ensure accuracy and control at the lower end a conventional flow meter would require very high tolerances for the valve components. The valve pin of the present invention avoids the need for such high tolerances, and therefore provides a solution that is cheaper and easier to manufacture, less susceptible to contamination, and less prone to mechanical failure.

In the case of a gas blender, the valve extends the accurate operating range of the device without the need to include an expensive pressure regulator. The importance of delivering an accurately and precisely controlled oxygen concentration from a medical gas blender to a patient has already been discussed.

In the case of the flow meter, which may already have the required accuracy, the valve provides a more user-friendly and/or cost-effective solution to that problem.

The valve comprises a valve pin with an elongate body with an outer sealing surface and a tapered part tapering towards a free end of the body. A sealing element surrounds the valve pin to provide a seal with the outer sealing surface at a defined sealing position, and relative movement of the valve pin and the sealing element away from the sealing position provides a variable flow area between the sealing element and the valve pin. The valve pin is shaped to increase the flow area of the valve close to the sealing position The elongate body of the valve pin may have a first portion of substantially constant cross-section, ie an untapered portion, and a second separate tapered portion towards the free end. A sealing position of the valve pin may be provided on the first portion.

A recess may be provided in the outer sealing surface of the body close to the sealing position. The recess may comprise an elongate slit or channel the length of which is aligned with the length of the elongate body, for example between the first and second portions of the elongate body.

The depth of the elongate slit, into the elongate body, may vary along the length of the slit. For example, the depth of the elongate slit may fluctuate or may reduce from the free end of the body towards the second end. The depth of the slit may flare towards the free end of the valve. The slit may extend so far that it is present in an end face of the valve pin defined by the free end of the body.

The width of the elongate slit may be constant along the length of the slit, or may vary. The width of the slit may reduce from the free end of the body towards the sealing position, and may flare towards the free end of the body. The slit may provide an open end section at the free end of the body The outer sealing surface may have a substantially constant cross-section, and the variation in depth of the elongate slit may provide the tapered part of the valve.

More than one slit or alternative recess may be provided. The form of multiple recesses on a single valve pin need not be consistent. For example, first and second elongate slits may be provided. The length of the first elongate slit may be greater than the length of the second elongate slit.

The invention also provides a valve pin for use in a flow controller such as a gas blender, the valve pin having an elongate body with an outer sealing surface and a taper towards a free end of the body, and wherein an elongate slit is provided in the outer sealing surface of the body between the free end and a second end of the elongate body, the length of the elongate slit being aligned with the length of the elongate body.

It will be understood that a flow controller such as a medical gas blender could be provided comprising a valve pin as described above. Accordingly, a further aspect of the invention provides a gas blender flow controller comprising an inlet for connection to a gas supply, an outlet, and a flow regulation valve between the inlet and the outlet, wherein the flow regulation valve comprises a valve pin having an elongate body with an outer sealing surface and a taper towards a free end of the body, and wherein an elongate slit or channel is provided in the outer sealing surface of the body between the free end and a second end of the elongate body, the length of the elongate slit being aligned with the length of the elongate body.

The invention may also provide a valve pin for a gas flow controller, wherein an outer surface of the valve pin comprises a recess close to a sealing position on the valve pin. Providing one or more recesses close to a sealing position allows one or more flow channels to be created along the valve pin. This can improve flow control, particularly at low-flow valve positions (ie positions close to the sealed position of the valve) when compared, for example, with a simple tapering of the valve pin. The recess may take different forms and multiple recesses may be provided, as discussed above. The invention may also provide a gas flow controller comprising an inlet for connection to a gas supply, an outlet, and a flow regulation valve between the inlet and the outlet for controlling flow of gas from a gas supply to the outlet, wherein the flow regulation valve comprises a valve pin as described.

The valve pin of the gas flow controller/blender may comprise one or more additional features as described above, and/or the gas blender may further comprise a linear stepper motor for moving the valve pin. Using a stepper motor provides certain advantages, for example regarding power consumption.

However, a servo motor or, indeed any other digital or analogue motor could alternatively be used to move the pin if required.

The flow controller or gas blender may, in particular, be used in a breathing circuit, for example in a hospital environment. Accordingly, the invention also provides a breathing circuit comprising a medical gas blender or a gas flow controller as previously described.

The gas flow controller and gas blenders described are designed to run directly off the gas pressure at the wall in the hospital, so there is no prior pressure regulation or pressure generation required. This makes the devices highly cost effective.

Wherever practicable, any of the essential or preferable features defined in relation to any one aspect of the invention may be applied to any further aspect.

Accordingly, the invention may comprise various alternative configurations of the features defined above.

Practicable embodiments of the present will now be described with reference to the accompanying drawings, of which:

Figure 1:
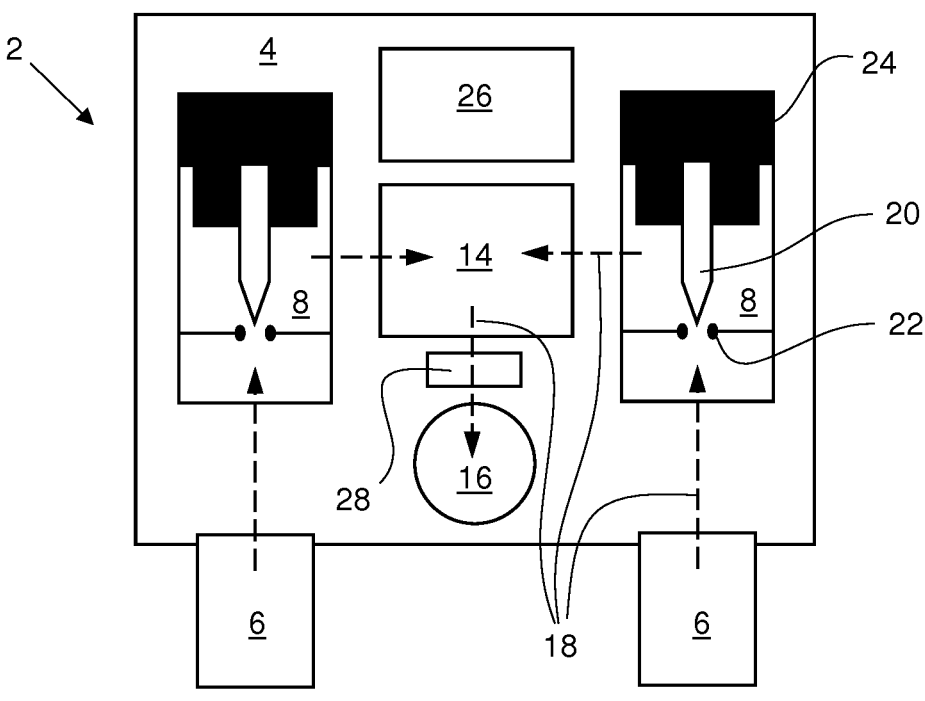
FIG. 1 is a schematic view of a gas flow controller according to a first embodiment of the invention.

A schematic view of a type of gas flow controller, specifically a medical gas blender 2 is shown in FIG. 1. The gas blender 2 briefly comprises a base housing 4 within which the various components of the gas blender 2 are housed. A pair of inlet fittings 6 are provided externally of the housing 4 for connection to gas supplies in a hospital or similar. One inlet fitting 6 connects, in use, to an oxygen source such as a supply of pure oxygen or 93% oxygen, and the other inlet fitting 6 connects to pressurised air. The connections are made using separate tubes or lines connected to the supply pressure, often provided at the wall of the hospital.

Each inlet fitting 6 is connected to a lower end of a valve housing 8. The two valve housings 8 are also connected to a mixing chamber 14 which is, in turn, connected to an outlet port 16 provided at the front of the housing 2. It will be understood that, in use, gas flow 18 passes from the inlet fittings 6 successively through the valve housings 8 and mixing chamber 14 before exiting the gas blender 2 through the outlet port 16. O-rings are provided at the various connection points to provide a gas-tight passageway.

The flow from the outlet port 16 can then be directed to a patient via standard tubes or lines. Other known components of respiratory circuits may be connected between the outlet port 16 and the patient if required.

The flow entering each valve housing 8 from its respective inlet 6 is regulated by a valve pin 20 which engages with a sealing O-ring 22. A linear stepper motor 24 is mounted to an upper end of each valve housing 8. The linear stepper motors 24 can be independently controlled to move the valve pins 20 towards or away from the sealing O-rings 22 to alter the cross-sectional area of each passageway, and thus control the flow between open and closed positions. The valve housings 8 and mixing chamber 14, together with the valve pins 20 and their respective motors 24 can therefore be considered a valve assembly or flow controller.

An oxygen sensor assembly 26 is provided for measuring the level of oxygen concentration in the mixing chamber 14 and/or flowing to the outlet port 16. This information can be used, possibly along with an oxygen saturation (SpO₂) reading taken from a patient, to automatically calculate the required concentration of oxygen to be delivered to the patient using a suitable algorithm and feedback control if required. The gas blender 2 can then respond to this automatically and independently adjust the position of each motor 24, and therefore its associated valve pin 20, to adjust both oxygen and air flow to a desired flow rate and oxygen concentration. The required gas mixture then flows out of the outlet port 16 at the desired flow rate and oxygen concentration. A flow sensor assembly 28 is also provided downstream of the mixing chamber 14.

Alternatively, or additionally, a clinician can adjust the oxygen concentration and flow manually based on the reading from the oxygen sensor 26 displayed on an LCD screen or similar display provided on the housing 4.

Using stepper motors 24 to actuate the valve pins 20 helps to minimise power drain during use. The motors 24 need only be activated when the valves need adjusting, so there is no power drain during steady flow situations. This also means that the blender 2 can continue to function at steady state even if a power supply is interrupted. A battery may be provided to maintain power to various parts of the unit during a power interruption, and to allow some movement of the stepper motors 24 if required to modify the gas flow.

Additional control accuracy and precision may also be provided by modulating between steps in the stepper motors 24, either by microstepping or a slow (0.5-5 second) pulse width modulation between two steps. Microstepping involves sending instructions to switch between the fixed steps of a stepper motor faster than the motor can respond, which results in the motor :hoveringˇin a position between fixed step points. A similar result can be achieved if the motor is told to repeatedly spend 0.5 seconds at one step and 0.5 seconds at the next step to produce a slow modulation and, in effect, a mid-position between the two steps.

In either case, appropriate control can effectively provide additional stop positions for the valve between the steps defined by the stepper motors 24, thus improving precision. This could be beneficial, for example, if a control algorithm outputs required concentration changes of around 0.5%-1% when the stepper motors 24 are only designed to achieve 1.4% steps. Although this level of precision will rarely be required in practice, the same theory could be used to generally permit the use of less precise stepper motors than would otherwise be necessary, thus reducing costs.

Figure 1A:
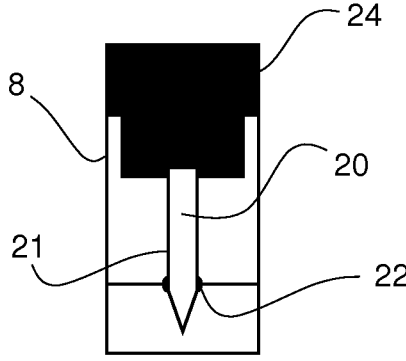
FIG. 1A is a schematic view showing a valve and housing of the flow controller in isolation.

FIG. 1A schematically shows a valve assembly from FIG. 1 in isolation. The valve is shown in a closed configuration with the valve pin 20 advanced to a sealing position where an outer surface 21 of the valve pin 20 forms a seal with the sealing O-ring 22. It will be understood that the valve arrangement shown in FIG. 1A, ie the valve housing 8, stepper motor 24, valve pin 20 and sealing element 22, could easily be incorporated into alternative flow controllers such as a flow meter if desired.

Figure 2:
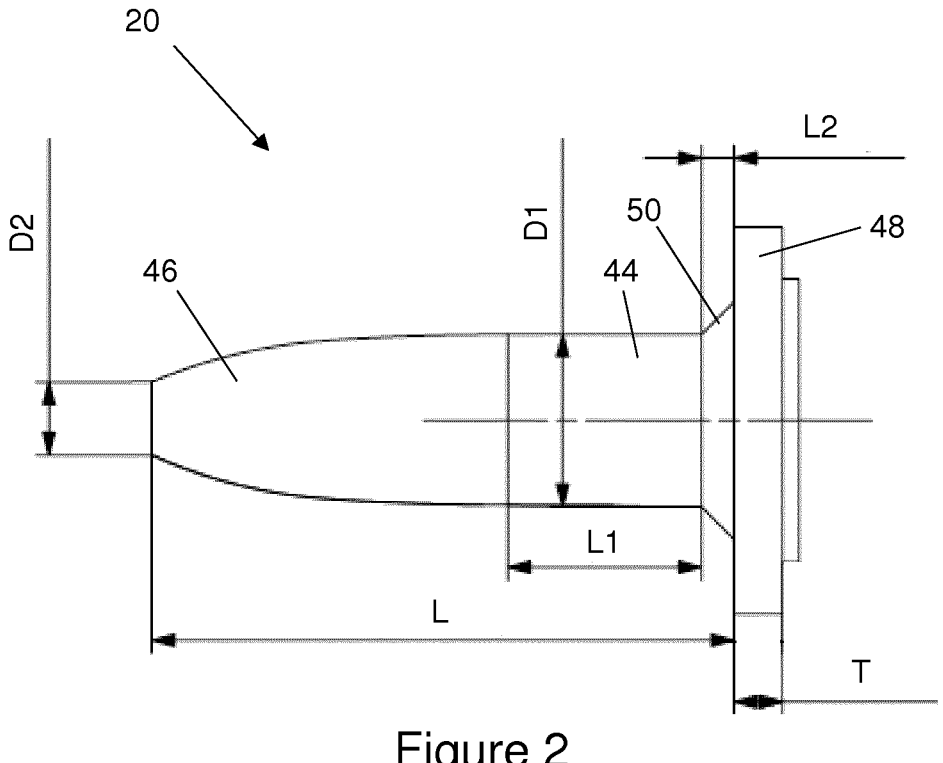
FIG. 2 is a side view of a valve pin from the gas flow controller of FIG. 1.

FIG. 2 shows a side view of a valve pin 20 from the gas blender 2 of FIG. 1. The valve pin 20 is generally :bullet shapedˇ, with a generally constant diameter stem portion 44 and a non-linearly tapering point 46 at a first end. A larger diameter base 48 is provided at a second end of the valve pin 20, opposite the tapered first end 46, for attachment to a linear motor 24.

In the illustrated example, the stem portion 44 extends over a length L1 of around 6 mm from the end of a short transition from the larger diameter base 48, and has an outer diameter D1 of 5.35 mm. The stem portion 44 adjacent the base 48 includes a sealing position, at which the valve pin may form a complete gas-tight seal with an external sealing element such as an o-ring or similar. The tapering point 46 has a non-linear taper from the other end of the generally constant diameter stem portion 44 down to an end diameter D2 of 2.3 mm. The overall length L of the valve pin 20 from the larger diameter base 48 to the end of the tapered point 46 is around 18 mm, including the 1 mm length L2 of the transition, and the thickness T of the base 48 is around 1.5 mm.

The use of valve pins 20 in the gas blender results in a simpler and more cost-effective valve assembly than using proportional solenoid valves or similar, and also allows the use of stepper motors for control, which provides further benefits as outlined above. However, problems were encountered when trying to maintain the required accuracy and precision that is provided by more complex ventilator based systems, particularly when operating at relatively high inlet pressures and low flow rates.

The bullet shape of the pin 20 helps to linearize the valve response, but problems still arise when operating at high pressures. In particular, a small change in the motor position when the pin 20 is close to the O-ring 22 can change the cross-sectional area of the valve dramatically, leading to a loss of control.

Tapered valve pins and linear motors are most commonly used for opening and closing valves in low pressure LPG systems, and a tapered pin tends to provide adequate flow control during normal use at low pressures. However, medical gas flow controllers such as the gas blender of FIG. 1 are required to provide precise flow control at all operating pressures up to at least 6 bar (87 psi, 600 kPa), and testing found that the required precision/fine control was not obtainable during testing with a standard tapered valve pin. The problem could be addressed by including a regulator upstream of the control valves, but this adds complexity to the system and is not desirable.

Figure 3:
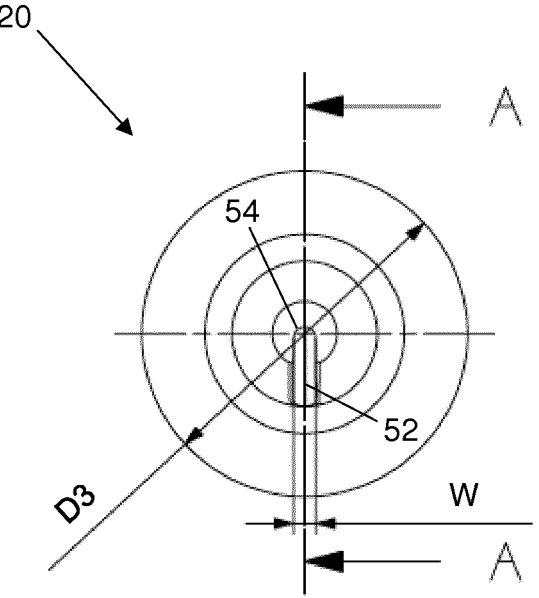
FIG. 3 is an end view of the valve pin of FIG. 2.

FIG. 3 shows an end view of the valve pin 20 from the end of the tapering point 46. To overcome the problems described above, a slit 52 or channel is provided in the side of the valve pin 20. The slit 52 has a curved floor 54 within the valve pin 20 and generally parallel spaced sides providing a width W of 0.8 mm.

Figure 3A:
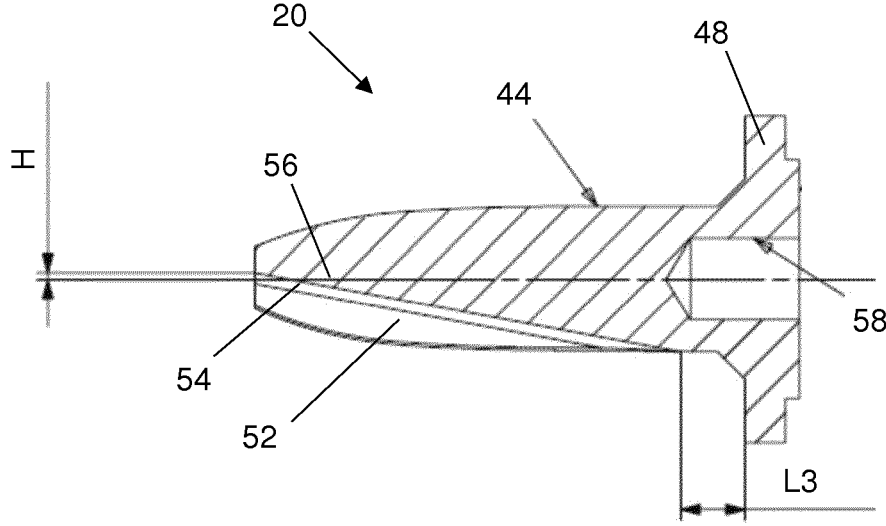
FIG. 3A is a cross-sectional view of the valve pin of FIGS. 2 and 3.

A cross-section of the valve pin 20 through the slit 52, as indicated by arrows A-A, is shown in FIG. 3A. The slit 52 can be seen to vary in depth along the length of the valve pin 20. At the end of the tapering point 46 the curved floor 54 of the slit 52, which has a height H of around 0.2 mm, extends just beyond the central axis 56 of the valve pin 20. As illustrated, the depth of the slit 52 decreases linearly along the length of the valve pin 20 towards the base 48, terminating part way along the constant diameter stem portion 44 at a distance L3 of around 2.4 mm from the base 48. Also shown in FIG. 3A is a central hole 58 in the base portion 48 for mounting the valve pin 20 to a motor 24.

The inclusion of the slit 52 in the side of the valve pin 20, and its varying depth along the length of the pin 20, allows greater control at high operating pressures. The slit 52 provides a path through the valve at a near-sealed position, and provides a larger cross-sectional area for the valve than would otherwise be the case when the pin 20 is close to the O-ring 22. At lower pressures and/or at higher flow rates, when the valve is more open, the effect of the slit 52 in the pin 20 is low, because the cross-sectional area of the valve is already so large.

Figure 4:
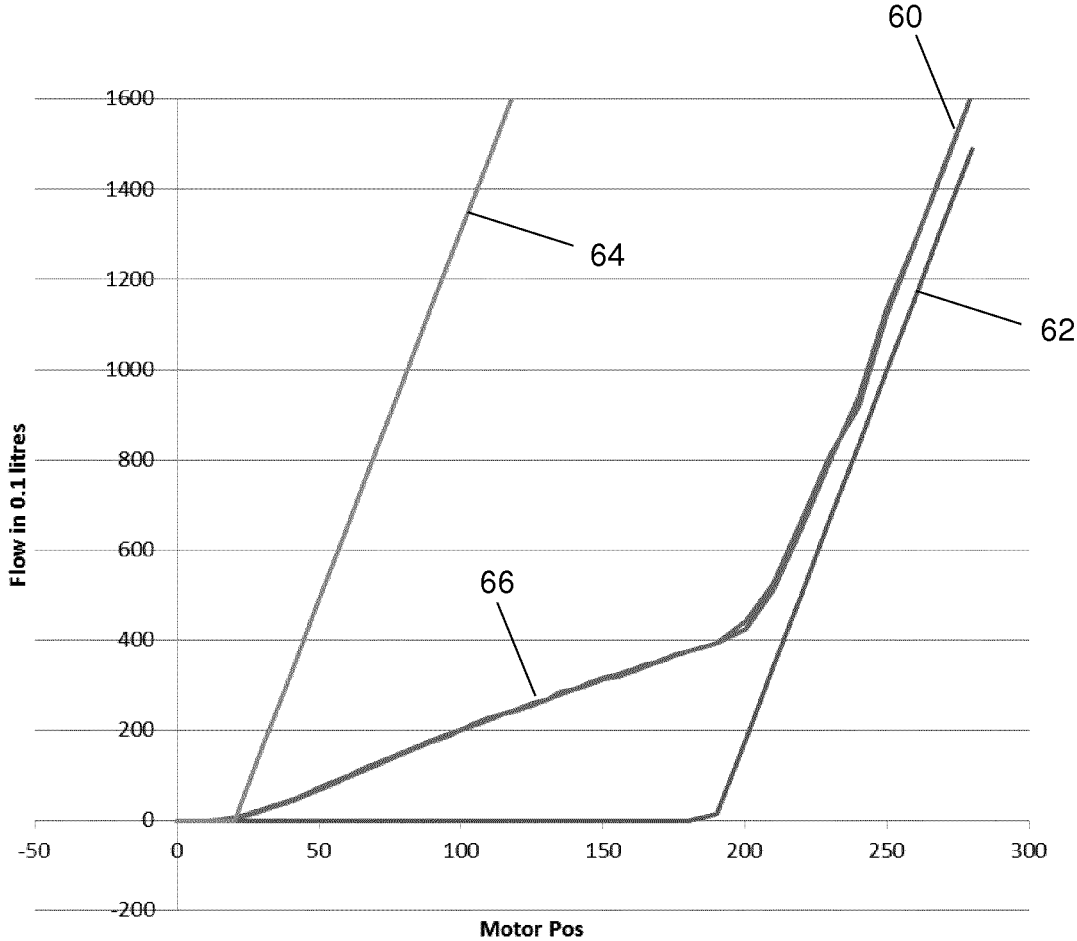
FIG. 4 is a graph showing comparative performance of three different valve pins at a set supply pressure.

FIG. 4 is a graph of motor position vs flow through a valve for three different valve pins. The middle plot 60 of the three illustrates the flow when using the slotted valve pin 20 as described above. To the right of the graph is a plot 62 illustrating the flow through a valve having a similar pin without the slit, while the leftmost plot 64 illustrates the performance of a shorter valve pin, specifically a pin with a shorter constant diameter stem portion 44, again without a slit. The bullet-shape of the valve pins provides the linear response seen in plots 62 and 64, and for the higher flow rates in plot 60.

At higher flow rates, above around 40 lmin$^{-1}$, it can be seen that all three valve pins provide very similar performance/response, specifically around 16.4 dl/step. Indeed, as shown the right-hand plot 62 has been offset from the Y axis to avoid overlap with the plot 60 for the slotted valve pin 20. Below 40 lmin$^{-1}$, however, the three plots 60,62,64 differ significantly.

Considering plot 62, for the similar bullet-shaped valve pin without a slit, the horizontal part of the plot indicates that most of the length of the bullet produces zero flow. The plot then abruptly steepens as the tapered part of the bullet is reached, so that a small change in motor position immediately produces a large change in gas flow (around 16.4 dl/step). As a result, a large amount of the motor range is effectively wasted, and the abrupt change then makes it impossible to select a precise low flow.

Shortening the length of the bullet addresses the first of these problems, as can be seen in plot 64 where far less of the motor range provides zero flow because the narrowing of the bullet shape would occur at lower opening positions. However, the abrupt change in flow rate caused by the tapered part of the bullet still provides the same difficulties when trying to precisely control low flow rates.

This problem is addressed by the provision of the slit 52 in the valve pin 20, as shown in plot 60. The lower part 66 of the plot 60 shows where the slit 52 is active, while the upper, steeper part is when the bullet shape takes over. Unlike the other plots 62,64, the slit 52 provides a relatively gradual increase of flow rate up to about 40 lmin$^{-1}$, before the same faster response is provided above this. This allows for more precision when low flows are required (more motor movement for a small change in flow), while still allowing for large flows with less precision. The difference can be quantified by comparing the gradients for the two parts of the plot. The lower part 66 has a gradient of about 2.4 dl/step, in comparison with around 16.4 dl/step for the upper part. This means that the motor must move approximately seven times (16.4/2.4) as far to provide the same flow change at low flow rates (<40 lmin$^{-1}$) than at higher flow rates, allowing far more precise control in this region.

Another benefit provided by the slit 52 is that the valve pin 20 becomes less reliant on the physical method of sealing between the casing and the needle/bullet. This physical sealing typically makes the actual opening point very unreliable, which further reduces the precision of typical valve pins at low flow rates.

The plots 60,62,64 of FIG. 4 all assume a supply pressure of around 4 bar, but flow reduces approximately linearly with pressure, so a different supply pressure would not significantly change the relationships shown.

Figure 5:
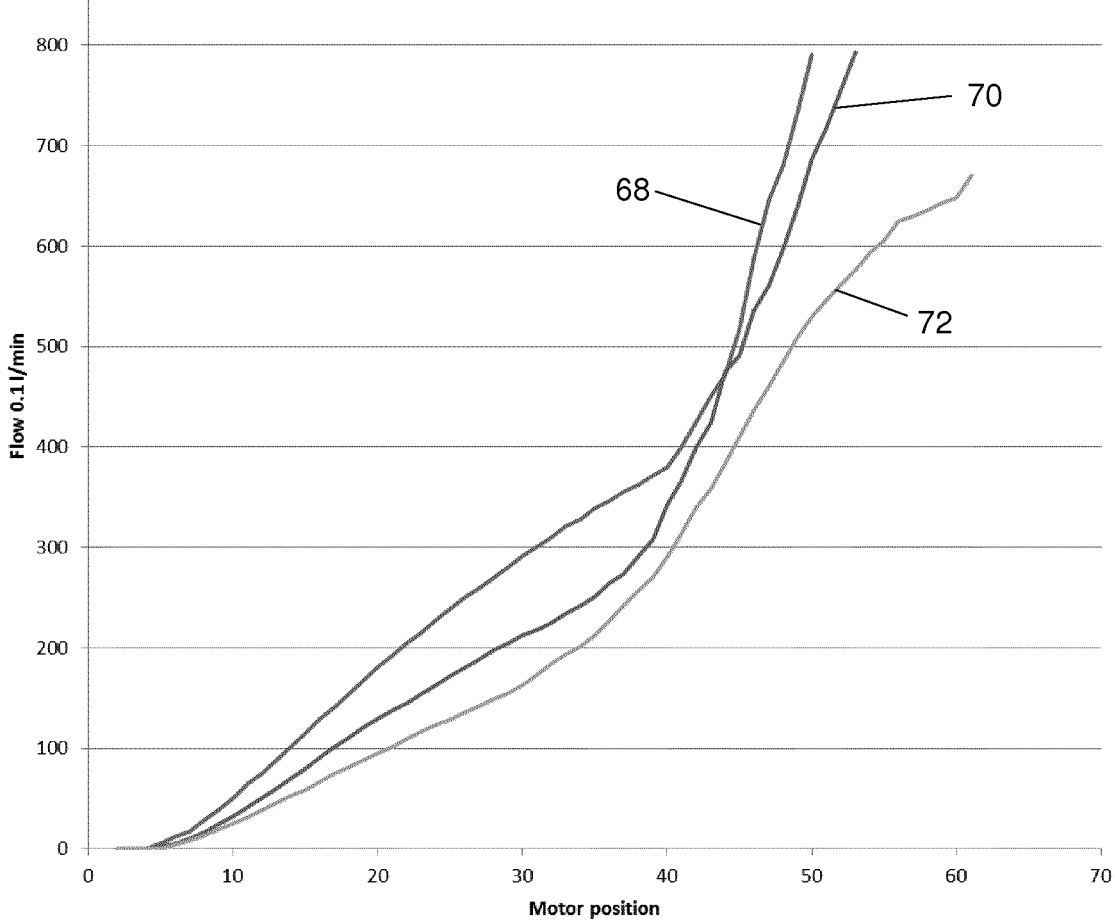
FIG. 5 is a graph showing the performance of the valve pin of FIGS. 1-3A at different supply pressures.

By way of example, FIG. 5 shows three overlaid plots showing the relationship between motor position and flow rate for the valve pin 20 at three different supply pressures. Plots 68 and 70 relate to supply pressures of 3.5 bar and 2.5 bar respectively, and both show predictable linear performance, similar to that seen in FIG. 4, in both regions of the graph (governed by the slit 52 and bullet shape). The third plot 72 relates to a lower supply pressure of 1.5 bar. This is below the normal required operating pressure range for gas blender applications (typically 2-6 bar, and rated to operate at up to 10 bar before failure), but still shows similar performance trends over the majority of the range shown. Indeed, results in testing found improvements for supply pressures as low as 0.5 bar.

By providing a valve pin 20 which provides finer control across a wide range of pressures, the described gas blender no longer needs to include a complex and costly flow regulator. The resulting device is thus simpler and more cost-effective.

Although the described embodiment provides a pin 20 with just a single slit 52, a pin may alternatively be provided with multiple slits, possibly of various depths and shapes. It should also be understood that alternative means of controlling or altering the cross-section of the pin could be provided.

As noted, the bullet shape of the valve pin 20 is beneficial in linearizing the valve response, but the additional control provided by the slit 52 would also be beneficial if applied to alternative valve pin shapes.

Figures 6, 7:
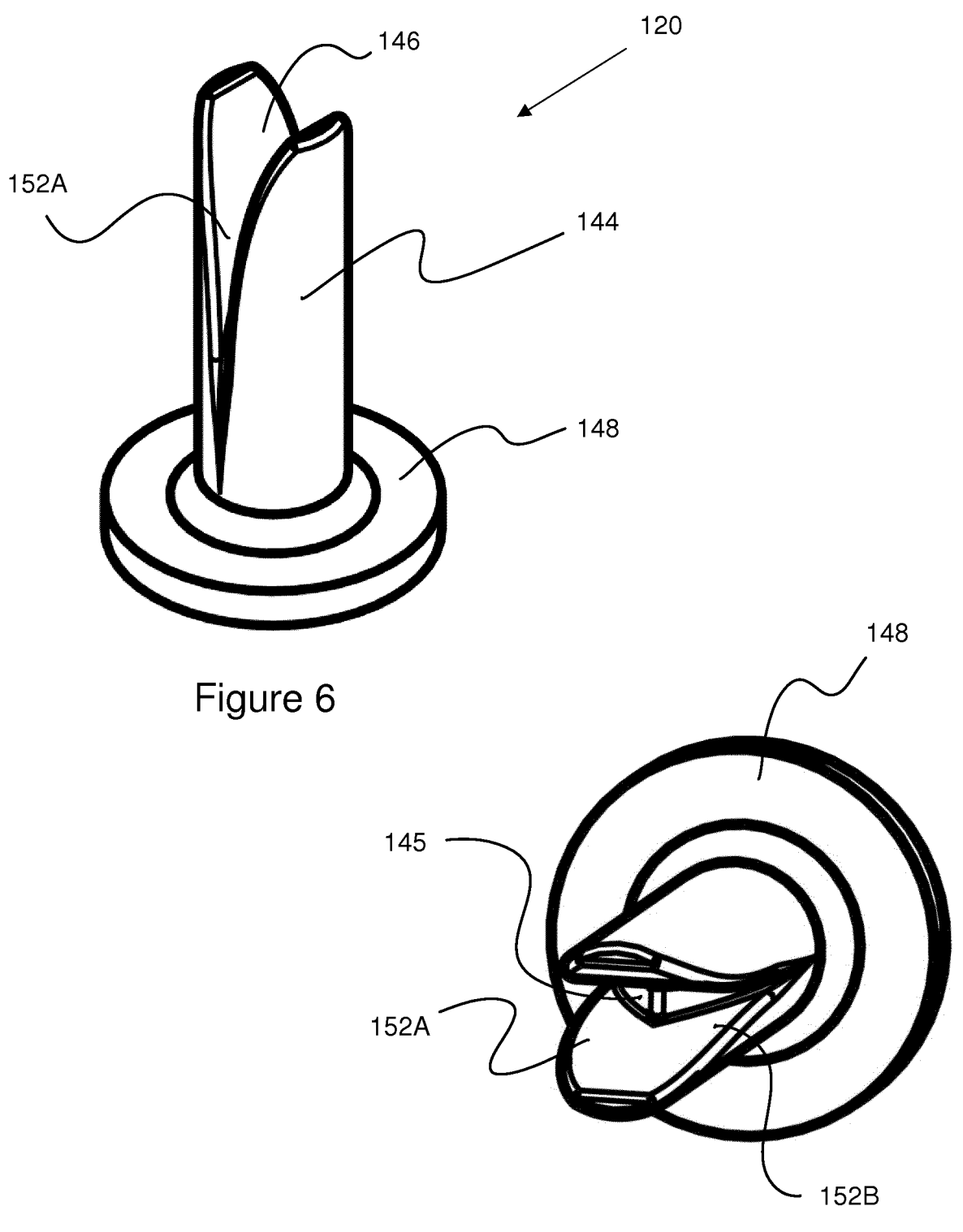
FIG. 6 is a first perspective view of an alternative valve pin.
FIG. 7 is a second perspective view of an alternative valve pin.

An alternative design of valve pin 120 is illustrated in FIGS. 6 to 9B. Unlike the valve pin 20 already described, the alternative valve pin does not comprise a taper 46 on the exterior of the body portion. Instead, the stem portion 144 comprises an open end section 146 provided by first and second slits or channels 152A,152B which widen and deepen as they extend from the larger diameter base 148, leaving a tapered central part 145 of the valve stem 144. This provides the alternative valve pin 120 with a :duckbill˜appearance, as can be seen in FIGS. 6 and 7.

Figure 8:
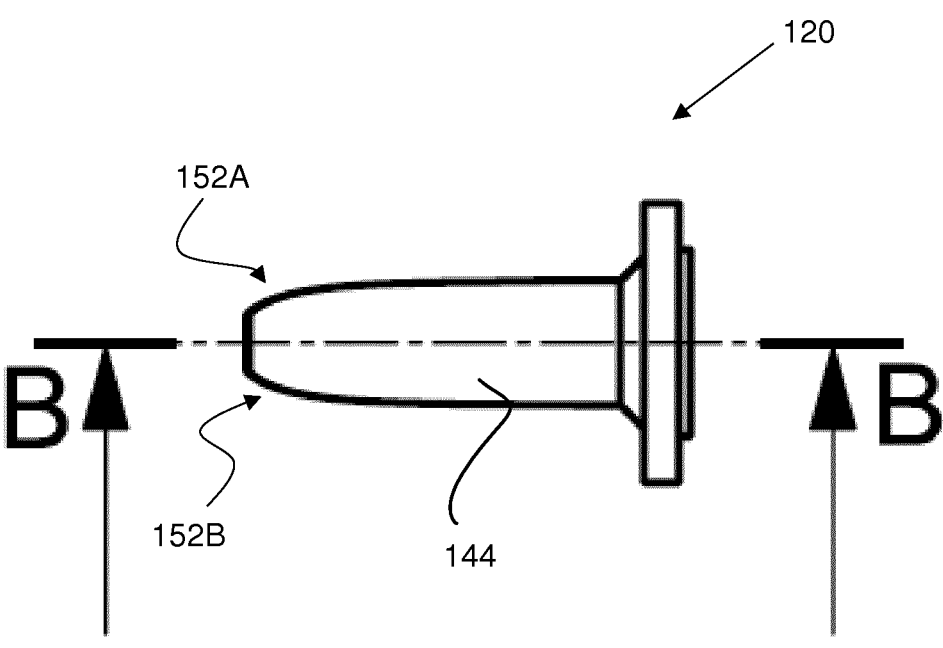
FIG. 8 is a front view of the valve pin of FIGS. 6 and 7.
Figure 8B:
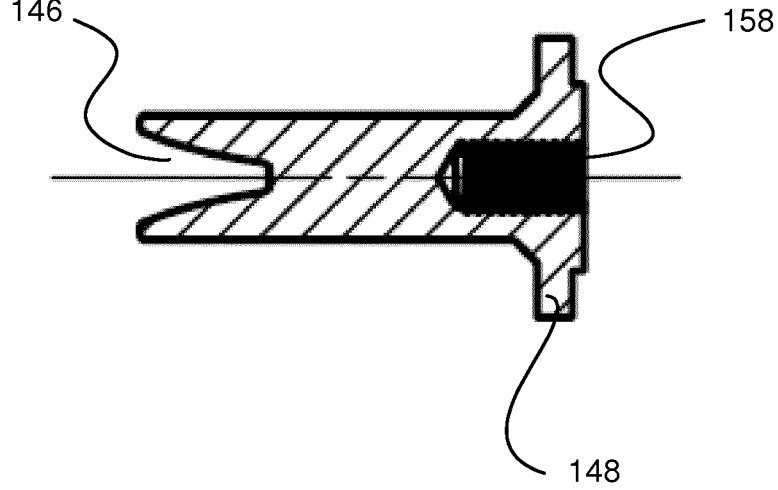
FIG. 8B is a cross-section view taken at the line B-B in FIG. 8.

A front view of the alternative valve pin 120 is shown in FIG. 8. The apparent taper at the end of the stem portion 144 is a result of the widening and deepening 152A,152B on either side of the valve stem 144. The open end 146 can clearly be seen in the cross-sectional view of FIG. 8B, which is taken at the line B-B in FIG. 8. The duckbill shape of the pin 120 is also clearly visible, as is a central hole 158 provided in the base portion 148 for mounting the valve pin 20 to a motor 24

Figure 9:
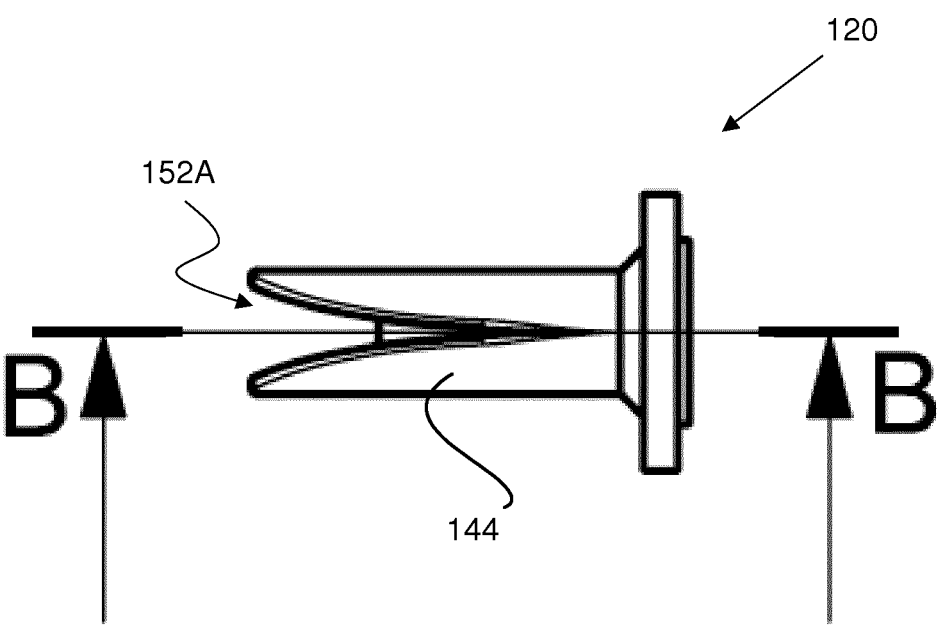
FIG. 9 is a side view of the valve pin of FIGS. 6 and 7.

FIG. 9 shows a side view of the alternative valve pin 120, in which the generally straight sides of the valve stem 144 and the flared shape of the first channel 152A can be seen. The alternative valve pin 120 was developed, at least in part, to address problems associated with the physical method of sealing between the previously described bullet-shaped valve pin 20 and an external o-ring seal. While the bullet-shaped valve pin 20 achieve a desirable linear response over a range of flows/pressures, some problems still arose at the point the pin separated from or moved off the o-ring. The generally constant outer diameter of the alternative pin 120 helps to keep the stem 144 in constant contact with an o-ring or similar seal. Indeed, the majority of the outer surface of the alternative pin 120 remains in contact with the o-ring right up to the point that it completely disengages. The variable flow area is provided by the flaring of the slits 152A,152B rather than by an external taper. FIG. 9 also indicates the location of the cross sectional view shown in FIG. 9B.

Figure 9B:
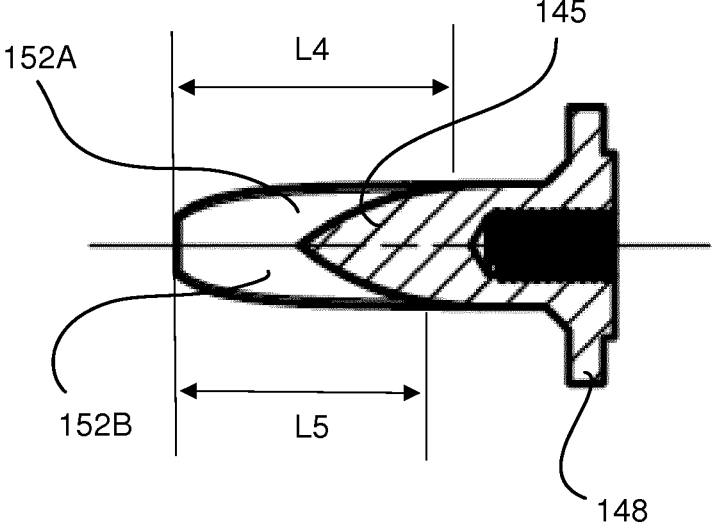
FIG. 9B is a cross-section view taken at the line B-B in FIG. 9.

The tapered shape of the central part 145 of the valve stem 144 can be seen in FIG. 9B. The curved taper in the illustrated example is provided by a flaring of the first and second channels 152A,152B as they deepen towards the end of the valve pin 120. It should be noted that alternative tapers, such as a straight taper, could be provided if the first and second channels 152A,152B were not flared as shown. The positions and sizes of the first and second channels 152A,152B may be substantially identical. However, in the illustrated example the total length L4 of the first channel 152A is greater than the total length L5 of the second channel 152B, meaning that the first channel 152B starts closer to the base portion 148 than the second channel 152B. As a result, when the alternative valve pin 120 is moved progressively away from a sealing position (located adjacent the base portion) during use, flow is permitted initially through the first channel 152A only, and then through both the first and second channels 152A,152B, and finally through the open end section 146 of the valve pin 120. Various paths are therefore through the alternative valve pin 120, including at a near-sealed position, and as with the valve pin 20 previously described this provides greater control and a more linear response at high operating pressures and/or low flow rates. The flaring of the first and second channels 152A,152B, and ultimately the open end section 146, provides a more open profile to the valve at lower pressures and/or at higher flow rates. Although the alternative valve pin 120 abruptly disengages from an o-ring/seal, due to its generally constant external diameter, the flared channels 152A,152B and open end section 146 mean that the valve is largely open at the point of disengagement. Any effect of the abrupt disengagement is therefore minimal, much in the same way that the influence of the slit 52 in the bullet-shaped valve pin 20 is lower when the valve is more open, as previously described.

The dimensions of the alternative valve pin 120 will typically be similar to the valve 20 previously described. For example, the length from the larger diameter base 148 to the end of the open end 146 will likely be around 18 mm. However, shorter valve pins could be provided, where a comparable dimension may be around 14 mm, either by reducing the overall size or by effectively cutting the open end section 146 shorter than shown.

Figure 10:
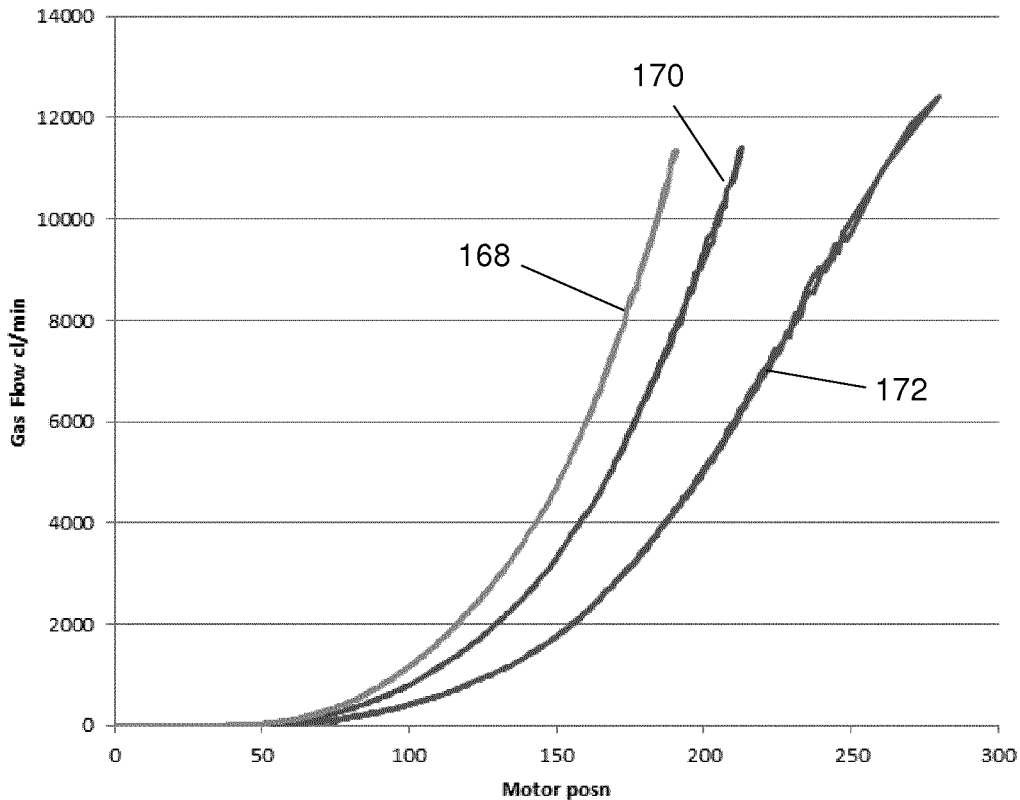
FIG. 10 is a graph showing the performance of the valve pin of FIGS. 6-9B at different supply pressures.

FIG. 10 shows three overlaid plots showing the relationship between motor position and flow rate for the alternative valve pin 120 at three different supply pressures. Plot 168 relates to a supply pressure of 6 bar, plot 170 to a supply pressure of 4 bar, and plot 172 to supply pressure of 2 bar. All three plots 160,170,172 show comparative performance, illustrating the predictability and suitability of the alternative valve pin 120 across the standard operating pressure range of 2-6 bar.

The valve pins 20,120 can be operated using linear stepper motors. This minimises the power drain of the system, because the motors need to be activated only when movement of the valve pin 20,120 is required, and means that the valves will remain in position, maintaining a desired flow rate, if power to the unit is interrupted.

The overall systems incorporating the new valve pins 20,120 provides the required level of precision in a dedicated system which avoids the unnecessary complexity found in many ventilators and removes the requirement for a regulator. The valve pins are described herein provide turndown ratios of 1500:1 and 5000:1, while also being relatively simple to manufacture. Alternative valve arrangements with a suitably high turndown ratio may, however, also provide similar benefits and allow implementation of the flow control and gas blender aspects of the invention.

For example, precision manufactured bell-shaped valves are available that claim to provide turndown ratios of around 10,000:1. As a further alternative, two precision manufactured rotating discs with appropriately shaped apertures to could, with suitably tight tolerances, provide the turndown ratio required to implement the invention. The rotating discs may be driven by stepper motors in the same way as the valve pins 20,120 already described.

Figure 11:
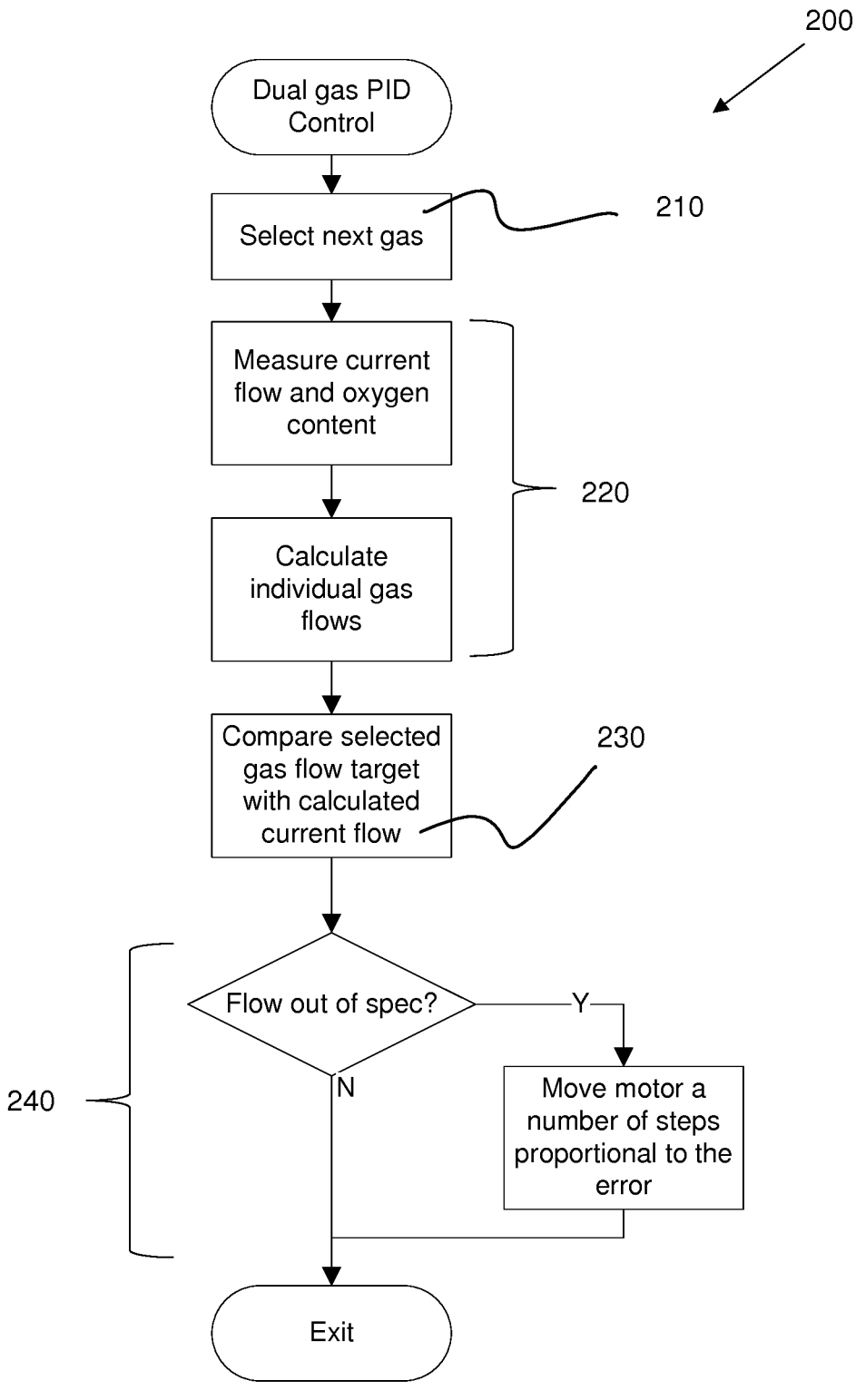
FIG. 11 is a flow chart showing a dual gas control loop to be implemented by a gas flow controller.
Figure 12:
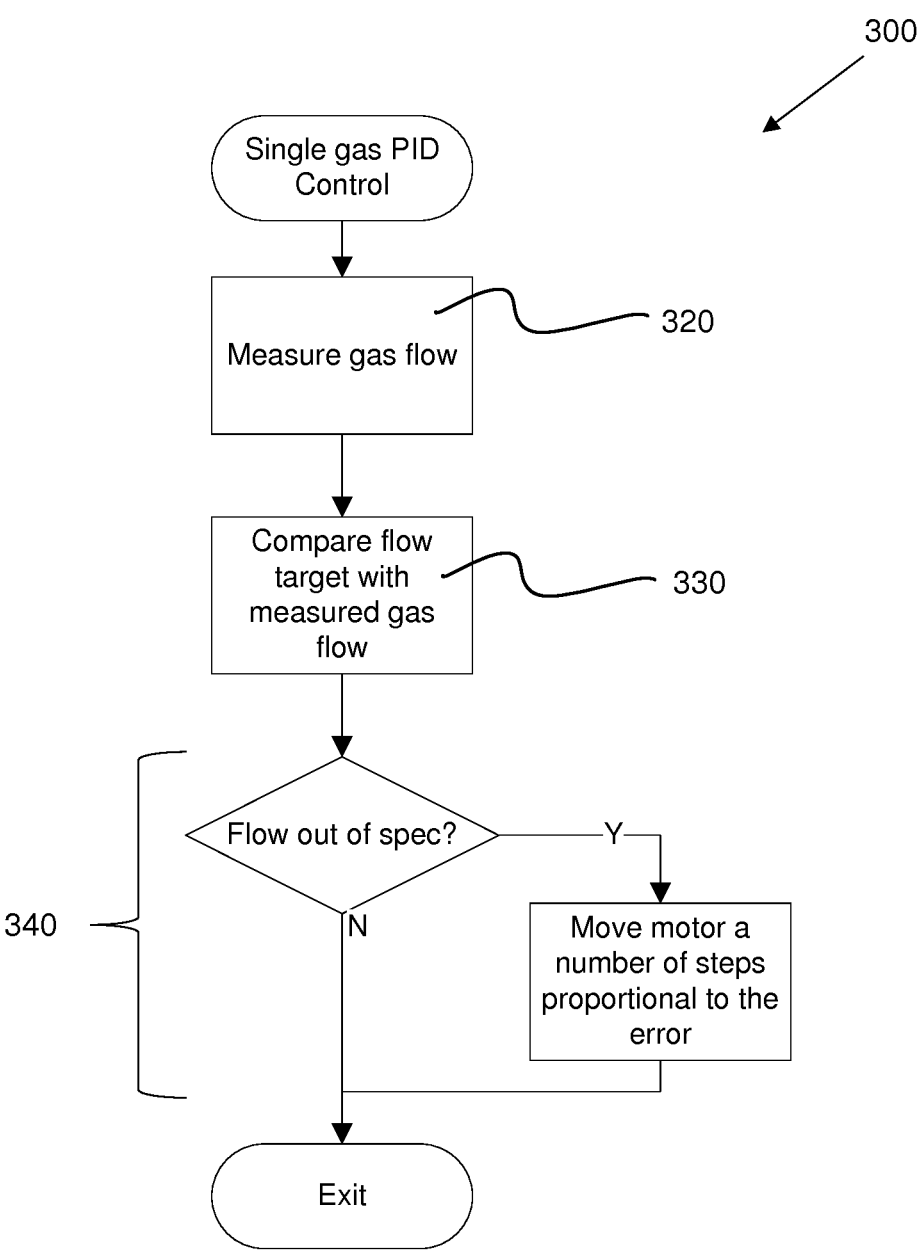
FIG. 12 is a flow chart showing a single gas control loop to be implemented by a gas flow controller.

FIGS. 11 and 12 are flow charts setting out elements of control strategies that are applicable to various aspects of the invention. The control strategies as shown are iterative in a closed loop.

FIG. 11 illustrates a suitable control strategy 200 for a gas blender according to the invention.

Control of the gas flow using, for example, a motorised valve pin 20,120 as previously described is done using a software-controlled stepper motor in a closed loop. The output flow is compared with the target flow 230 and the difference is used to modify the position of the pin 240, thus changing the output flow.

In use, the gas blender controls two gasses independently to achieve a selected flow and oxygen concentration, with each gas being checked in turn against the target flow for that gas. The control method 200 therefore first selects a gas for measurement 210 before implementing analysis 220 and comparison 230 steps and controlling a motor based on the comparison 240.

During development, it was found suitable for the control loop to be executed every 200 ms, to suit the speed of a flow sensor used in a particular medical gas blender. However, it will be understood that different repeat rates/frequencies could be used depending on the needs of a particular flow sensor and/or of a particular flow control device.

A similar control method can also be used to measure and control the flow of a single gas, for example in a medical flowmeter/regulator, as illustrated in FIG. 12. The flowchart of FIG. 12 shows a simplified method 300 including the steps of measuring a gas flow 320 and comparing with a target value 330. As in the control method 200 of FIG. 10, a motor is then moved a number of steps based on the comparison 340. Again, this is executed every 200 ms, or at a different frequency if a particular application requires.

Although illustrated as incorporating a Proportional-Integral-Differential (PID) controller, the control strategies 200, 300 of FIGS. 11 and 12 would still function if only the proportional element were used. The number of steps that the motor should move 240,340 is calculated from a mix of the flow error, multiplied by an empirically determined 'Proportional Constant_(Kp). This constant effectively calibrates for the mechanical scaling from the incoming gas, through the motorised pin aperture and out of the device. The addition of an 'Integral Constant_(Ki), again calculated empirically, would help to speed up motion toward the target flow.

A further simplified version of the control loop/method 300 could be provided. Instead of moving the motor a number of steps proportional to the error at 340, it would be possible to just move the motor one step and measure again, moving one further step if the error hasn't been corrected. The simplification comes at the expense of a slower response time.

The invention claimed is:

1. A valve for use in a medical gas flow controller, the valve comprising:

a valve pin having an elongate body with an outer sealing surface having a substantially constant cross-section, and a sealing element surrounding the valve pin to provide a seal with the outer sealing surface at a defined sealing position, wherein relative movement of the valve pin and the sealing element away from the sealing position provides a variable flow area between the sealing element and the valve pin, the valve pin having a recess in the outer sealing surface of the body close to the sealing position to increase the flow area of the valve close to the sealing position, wherein the recess comprises an elongate slit, the length of the elongate slit being aligned with the length of the elongate body, the valve pin further comprising a tapered part, having a non-linear or curved taper, located within the elongate slit on an interior portion of the elongate body and tapering in a direction from the sealing element toward a free end of the elongate body such that the elongate slit has a variable depth along the length thereof based on the tapered part of the valve pin.

2. The valve according to claim 1, wherein the depth of the elongate slit reduces from the free end of the body towards the sealing position.

3. The valve according to claim 1, wherein the elongate body of the valve pin has a first portion of substantially constant cross-section and a second separate portion tapered towards the free end to provide the tapered part, and wherein the sealing position is provided on the first portion, and wherein the elongate slit extends between the first and second portions of the elongate body.

4. The valve according to claim 3, wherein the slit is provided in an end face of the valve pin defined by the free end of the body.

5. The valve according to claim 1, wherein the elongate slit provides an open end section at the free end of the body.

6. The valve according to claim 1, wherein the width of the elongate slit reduces from the free end of the body towards the sealing position.

7. The valve according to claim 1, wherein the elongate slit comprises a first elongate slit and wherein a second elongate is also provided.

8. The valve according to claim 7, wherein the length of the first elongate slit is greater than the length of the second elongate slit.

9. The valve according to claim 1, wherein the width of the elongate slit reduces from the free end of the body towards the sealing position.

10. A medical gas blender comprising:

a first inlet for connection to a first gas supply, a second inlet for connection to a second gas supply;

a mixing chamber;

first and second flow regulation valves according to claim 1, wherein the first flow regulation valve is located between the first inlet and the mixing chamber for controlling the flow of a first gas to the mixing chamber and wherein the second flow regulation valve is located between the second inlet and the mixing chamber for controlling the flow of a second gas to the mixing chamber;

an outlet and control hardware for controlling the operation of at least one of the first and second flow regulation valves;

wherein the first and second flow regulations valves each have a turndown ratio in excess of 1000:1.

11. The medical gas blender according to claim 10, wherein the control hardware is configured to perform a measuring step, in which a gas flow is measured, and a comparison step, in which the measured gas flow is compared with a target flow.

12. The medical gas blender according to claim 11, wherein the control hardware is configured to select a gas flow prior to the measuring step.

13. The medical gas blender according to claim 11, wherein the control hardware is configured to additionally measure oxygen content and calculate individual gas flows as part of the measuring step.

14. The medical gas blender according to claim 13, wherein the valve pin of at least one of the first and second flow regulation valves is driven by a motor, and wherein the control hardware is configured to move the motor based on the outcome of the comparison step.

15. The medical gas blender according to claim 10, wherein first and second elongate slits are provided.

16. The medical gas blender according to claim 15, wherein the length of the first elongate slit is greater than the length of the second elongate slit.

17. A respiratory circuit comprising the medical gas blender according to claim 10.

18. A gas flow controller comprising an inlet for connection to a gas supply, an outlet, and a flow regulation valve according to claim 1 between the inlet and the outlet for controlling flow of gas from the gas supply to the outlet to adjust the gas flow at the outlet through a range of flow rates or pressures.

19. The gas flow controller according to claim 18, further comprising a linear stepper motor connected to the valve pin for moving the valve pin relative to the sealing element.

20. A medical gas blender comprising a gas flow controller according to claim 18, and further comprising a mixing chamber, wherein the flow regulation valve is located between an inlet and the mixing chamber for controlling the flow of gas to the mixing chamber.

21. The medical gas blender according to claim 20, wherein two flow regulation valves are provided, each flow regulation valve being located between an inlet and the mixing chamber, and each flow regulation valve comprising the valve pin and the sealing element surrounding the valve pin to provide a seal between the sealing element and the valve pin at a sealing position on the valve pin, and wherein relative movement of the valve pin and the sealing element away from the sealing position adjusts the gas flow through a range of flow rates or pressures.

22. The medical gas blender according to claim 20, further comprising an oxygen sensor.

23. The medical gas blender according to claim 20, further comprising control hardware.

24. The medical gas blender according to claim 23, wherein the control hardware comprises a feedback loop.

* * * * *